United States Patent
Heim

[19]

[11] Patent Number: 5,807,341
[45] Date of Patent: Sep. 15, 1998

[54] MEDICAL CATHETER DRESSING DEVICE

[75] Inventor: Warren P. Heim, Boulder, Colo.

[73] Assignee: Team Medical LLC, Boulder, Colo.

[21] Appl. No.: 764,601

[22] Filed: Dec. 11, 1996

[51] Int. Cl.[6] .................................................. A61M 25/00
[52] U.S. Cl. .......................................... 604/174; 604/180
[58] Field of Search .................................. 604/174, 180;
128/849, 852, 853, 854

[56] References Cited

U.S. PATENT DOCUMENTS

| | | | |
|---|---|---|---|
| 3,487,837 | 1/1970 | Peterson | 128/349 |
| 4,221,215 | 9/1980 | Mandelbaum | 128/155 |
| 4,392,857 | 7/1983 | Beran | 604/179 |
| 4,519,793 | 5/1985 | Galindo | 604/180 |
| 4,543,100 | 9/1985 | Brodsky | 604/180 |
| 4,903,710 | 2/1990 | Jessamine et al. | 128/849 |
| 4,959,055 | 9/1990 | Hillyer | 604/180 X |
| 5,263,939 | 11/1993 | Wortrich | 604/174 |
| 5,352,211 | 10/1994 | Merskelly | 604/180 |
| 5,364,367 | 11/1994 | Banks et al. | 604/180 X |
| 5,375,588 | 12/1994 | Yoon | 604/180 X |
| 5,429,608 | 7/1995 | Rom et al. | 604/163 |
| 5,449,340 | 9/1995 | Tollini | 602/58 |

OTHER PUBLICATIONS

"Directions for Use" for CONTAIN–OR™, Model Code #19000 and #19005, by DLP, Inc., Copyright 1993.
Product brochure by DLP, Inc. entitled "Infection Protection in a Nutshell" regarding CONTAIN–OR#, Copyright 1994.

*Primary Examiner*—Sam Rimell
*Attorney, Agent, or Firm*—Sheridan Ross P.C.

[57] ABSTRACT

A medical apparatus and method for managing one or more conveyance tubes used to inject or remove fluids, solids or semi-solids from a patient's body without the need for sutures. The device further includes a biohazard control system to reduce the risk of exposure of the medical biohazards such as blood and tissue to attending medical personnel.

30 Claims, 8 Drawing Sheets

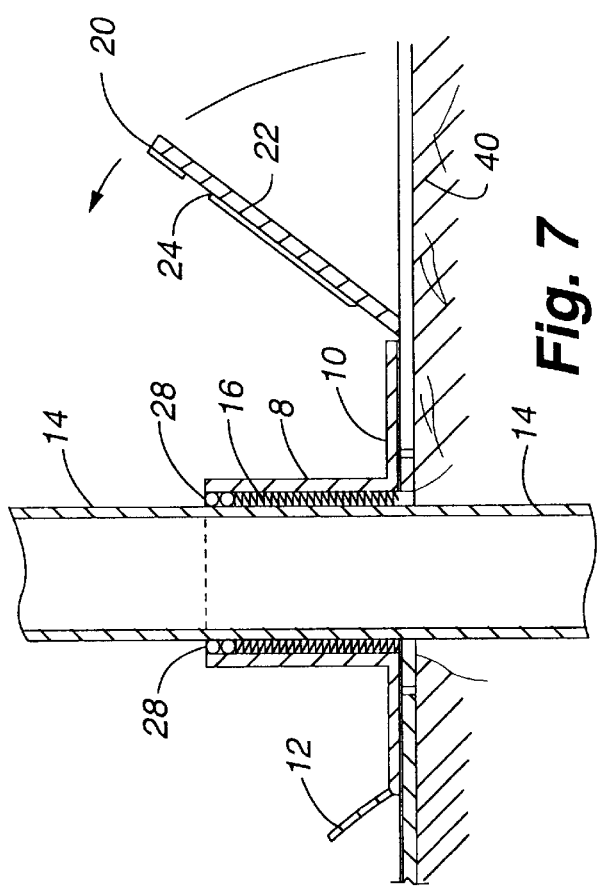
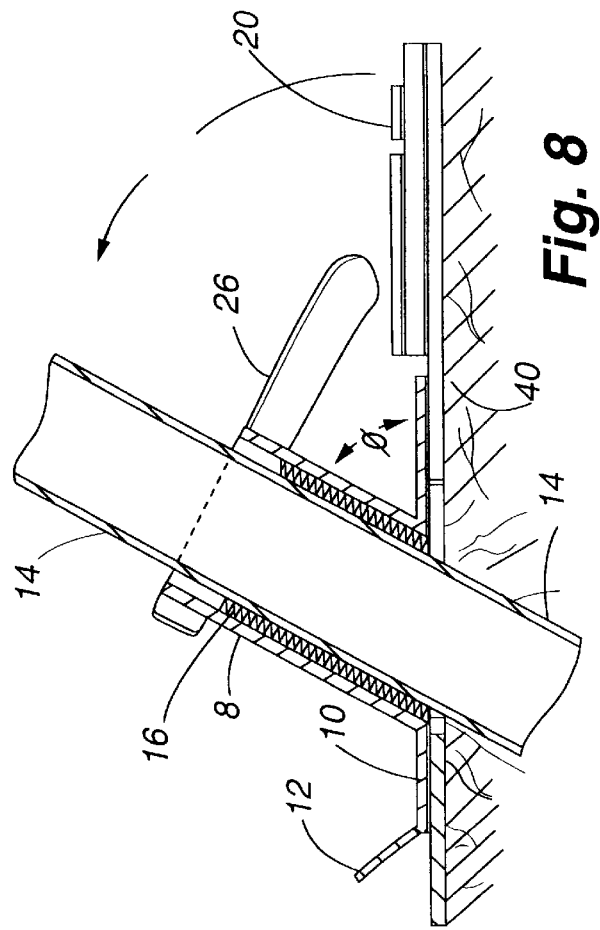

MEDICAL CATHETER DRESSING DEVICE

FIELD OF THE INVENTION

The present invention relates to an apparatus and method for managing medical conveyance tubes used to remove and/or introduce fluids or solids to/from a patient's body, and more particularly to contain medical biohazards associated therewith in a confined space.

BACKGROUND OF THE INVENTION

Conveyance tubes such as catheters are utilized in a variety of medical procedures to inject or remove fluids, gases and/or solids from a patient's body. For example, thoracic catheters are used to drain fluids, solids, and semi-solids from the mediastinal and pleural chest cavities to remove pressure on the lungs. For injection purposes, percutaneous indwelling catheters and other similar devices are used to introduce blood and other intravenous fluids into a patient's body.

To utilize the aforementioned conveyance tubes in body cavities, it is necessary for the attending physician to make an incision into the patient's skin and desired body cavity for insertion of the conveyance tube. Typically, the conveyance tube is then temporarily sutured directly to the patient's surrounding tissue to anchor the tube to the patient to prevent excessive movement or inadvertent withdrawal of the conveyance tube. This procedure is painful to the patient, time consuming and requires monitoring by medical personnel to assure that the sutures and conveyance tube remain in place.

During the removal of the inlet end of the conveyance tube from the patient's body cavity, there is commonly a discharge from the conveyance tube of medical biohazards. This discharge may include the fluids being injected or removed through the conveyance tube as well as blood and other medical biohazards which are present in the patient's body. Exposure to these uncontained biohazardous materials is potentially dangerous to attending medical personnel due to the possibility of acquiring Acquired Immune Deficiency Syndrome (AIDS), hepatitis, and other potentially infectious diseases carried in bodily fluids. Likewise, disposal of the biohazards is problematic to medical personnel without the ability to contain the biohazardous materials in a contained, transportable space.

Upon removal of the conveyance tube it is typically necessary for the attending physician or nurse to close the access wound in the patient's body with sutures, staples, or other similar devices. The wound must generally be cleaned, medicated and continually monitored to prevent infection and assure proper healing. This procedure requires the changing of bandages and other dressings on a timely basis, which is expensive and does not facilitate monitoring the wound without completely removing and replacing the dressings.

SUMMARY OF THE INVENTION

Accordingly, it is a primary object of the present invention to provide a method and assembly for supporting and managing one or more body conveyance tubes inserted in a patient's body which enhances a patient's comfort, is readily applied to and removed from the patient's body and is anchored to a patient's body without wound closing devices. In this regard, it is possible to supportably anchor the body conveyance tube to a patient's body without the need for sutures, staples, or other wound closing devices interconnected to surrounding tissue. It is a further object of the present invention to provide an enhanced dressing assembly which contains the medical biohazards associated with the use of body conveyance tubes within a predetermined confined space, thus reducing the safety risks to attending medical personnel. In the present context, the term "patient" refers to both human beings and other mammals such as horses and dogs and thus the disclosed apparatus and method may be used in both medical and veterinary applications.

To realize one or more of the noted objectives as well as other advantages, a medical dressing assembly is provided which includes an anchoring mechanism to support the body conveyance tube to the patient's body without the need for sutures. The assembly is multifunctional and hence eliminates the need to have separate components to achieve the noted goals of anchoring a conveyance tube to a patient's body, containing medical biohazards associated therein and applying a sterile dressing to the patient's access wound.

The aforementioned assembly comprises a dressing pad selectably attachable to a patient's skin adjacent an access wound or incision. The access wound provides a point of penetration for the conveyance tube. An upstanding, substantially rigid retaining collar is removably interconnected to a top surface of the dressing pad, and utilizes an interconnection means for supportable interconnection to the conveyance tube. The upstanding retaining collar may additionally have a plurality of longitudinal slots oriented in the collar to allow the collar to operatively collapse around the conveyance tube. Thus, the dressing pad in combination with the upstanding retaining collar and interconnection means provides sufficient support to anchor and stabilize the conveyance tube to the patient's body without the need for sutures, staples, or other tissue penetrating means.

By way of example, in one embodiment medical tape may be tightly wrapped around the retaining collar to temporarily interconnect the conveyance tube to the retaining collar. In an alternative embodiment one or more O-rings or other similar support devices may be used to stabilize the conveyance tube within the upstanding retaining collar. The o-ring is preferably positioned proximate the interior surface of the upstanding collar and frictionally engages an external surface of the conveyance tube to inhibit unwanted movement.

Although the retaining collar generally extends in a direction substantially perpendicular to a planar surface of the dressing pad, in some circumstances a less pronounced angle may be preferable. For example, when percutaneous indwelling catheters are used for injection purposes into a patient's artery or vein, less stress may be applied to the conveyance tube and surrounding tissue by utilizing a retaining collar with a slight angle. Thus, the retaining collar may be positioned at an angle of less than about 90 degrees as measured from a horizontal plane parallel to the dressing pad. More preferably, the retaining collar may have an angle of between about 25 degrees and 75 degrees as measured from a horizontal plane parallel to the dressing pad.

In a further embodiment of the present invention, an outwardly extensible biohazard control sleeve is utilized to substantially contain fluids such as blood or other medical biohazards within a confined space to inhibit exposure to attending medical personnel. Preferably, the biohazard control sleeve is interconnected on a first end to the dressing pad proximate the access wound, while extendably positioned within the upstanding retaining collar. The conveyance tube is positioned through both the confines of the biohazard control sleeve and the retaining collar and is enclosed by the biohazard control sleeve. Following the introduction or removal of fluids or solids to/from the patient's body through one or more conveyance tubes, the inlet end of the conveyance tube is removed from the patient's body. As the conveyance tube is withdrawn from the access wound, the biohazard control sleeve is simultaneously extended outwardly and away from the patient's body with the conveyance tube to substantially contain most medical biohazard discharge from either the conveyance tube or from the access wound in the patient's body. This containment significantly reduces the risk of medical biohazards coming in direct contact with attending doctors, nurses, and technicians, thus reducing the risk of exposure to infectious diseases carried in blood, tissue and other body matter.

The biohazard control sleeve may be constructed from an extensible, non-permeable pleated material such as polyvinyl chloride or polyolefin. This material, or other similar materials are capable of being extended, for example, in a pleated, fold out, accordion type fashion to many times their original length. This extendibility feature allows the biohazard control sleeve to be temporarily stored within the upstanding collar, yet extended upward a distance four to twenty times the original length of the upstanding collar. This assures that most or all of the conveyance tube which was inserted into the patient's body is adequately contained by the control sleeve.

In one embodiment the biohazard control sleeve has a drawstring, clip or other means for holding either the top end, bottom end, or both ends of the biohazard control sleeve in a secured position around the conveyance tube to help contain any medical biohazards. The biohazard control sleeve is then removed from the dressing pad by cutting the tube at a location near the dressing pad, or alternatively by the use of a perforated disconnection tab located on the dressing pad proximate the access wound.

To facilitate the extension of the biohazard control sleeve with the removal of the conveyance tube, the upstanding collar may be temporarily and removably interconnected to a top surface of the dressing pad. This may be accomplished with a pressure sensitive adhesive, hook and loop type material, or other interconnection means. Furthermore, to assist in the disengagement of the upstanding collar from the dressing pad, one or more pull tabs may be interconnected to the retaining collar support ring which extends parallel to the top surface of the dressing pad.

In another embodiment of the present invention a cover flap is provided to promote healing of the access wound upon removal of the conveyance tube from the patient's body. The cover flap is preferably hingably interconnected on one edge to a top surface of the dressing pad. Upon removal of the upstanding collar and biohazard control sleeve from the dressing pad, the access wound is exposed through an aperture in the dressing pad. The access wound is typically closed with sutures or staples and cleaned to help prevent infection. The cover flap may then be extended over the access wound and secured to the top surface of the dressing pad with a pressure sensitive adhesive material, a hook and loop type material, or other similar removable interconnection means. The cover flap may be temporarily disconnected or pulled away from the access wound as required to monitor the healing of the access wound. Additionally, sterile replacement cover flaps may be used as needed, and may include an impregnated medicated ointment to promote healing.

In application, a method for utilizing the dressing pad assembly is achieved by the physician first making an incision in a patient's body to create one or more access wounds for insertion of one or more conveyance tubes. The inlet end of the conveyance tube is then inserted through the access wound into a patient's body cavity, vein, or artery depending on the particular application. The dressing pad assembly is then positioned around the conveyance tube by means of a slot, or alternatively by inserting the exit end of the conveyance tube through an aperture in the dressing pad assembly and the attached retaining ring. Once properly positioned, the bottom surface of the dressing pad is secured to the skin of the patient, preferably with an adhesive. The retaining collar is then secured to the conveyance tube with medical tape or preferably using an attachment means which is integral to the retaining collar, such as medical tape that has a removable release liner, or other type of material which frictionally engages the conveyance tube to inhibit movement. The conveyance tube is then used for its intended purpose, i.e., for the injection or removal of fluids, solids or semi-solids into or from the patient's body.

Upon removal of the conveyance tube from the patient's body through the access wound, the biohazard control sleeve is simultaneously and progressively extended away from the access opening in the patient's body. Thus, as the inlet end of the conveyance tube is removed from the access wound, any medical biohazards discharged either from the patient's access wound or from within the conveyance tube can be contained within the biohazard control sleeve. Thus, the risk of exposure to medical personnel is significantly reduced.

To facilitate the removal of the upstanding retaining collar and biohazard control sleeve from the dressing pad, a pull tab may be used to disengage the retaining collar from the top surface of the dressing pad. The retaining collar is interconnected to a support ring which is removably interconnected to the dressing pad with a pressure sensitive adhesive material or hook and loop type material such as Velcro™. Once the biohazard control sleeve is adequately extended to contain the body conveyance tube, the biohazard control sleeve is cut near the dressing pad with a knife or scissors. Alternatively, the biohazard control sleeve may be disengaged from the dressing paid with a perforated tear surface.

In a further embodiment of the aforementioned method, either one or both ends of the biohazard control sleeve is closed with a drawstring, clip, or other similar means to substantially capture medical biohazards inside the biohazard control sleeve. The drawstring or clip may be permanently interconnected to the biohazard control sleeve, or provided separately. This step additionally reduces the probability of medical personnel becoming exposed to medical biohazards.

Upon complete removal of the conveyance tube, retaining collar and biohazard control sleeve from the dressing pad, the access wound is left exposed for proper cleaning. The physician then prepares the wound for proper healing and to prevent infection, by closing the wound with sutures or staples. In a further embodiment, a sterile cover flap may then be extended over the access wound to inhibit infection and promote healing.

BRIEF DESCRIPTION OF THE DRAWINGS

FIG. 7 is a cross-sectional view of the medical catheter dressing device showing an alternative embodiment for interconnecting the retaining collar and conveyance tube;

FIG. 8 is a cross-sectional view of the medical catheter dressing device depicting the retaining collar at an acute angle in relationship to the dressing pad.

DETAILED DESCRIPTION OF THE PREFERRED EMBODIMENT

Figure 1:
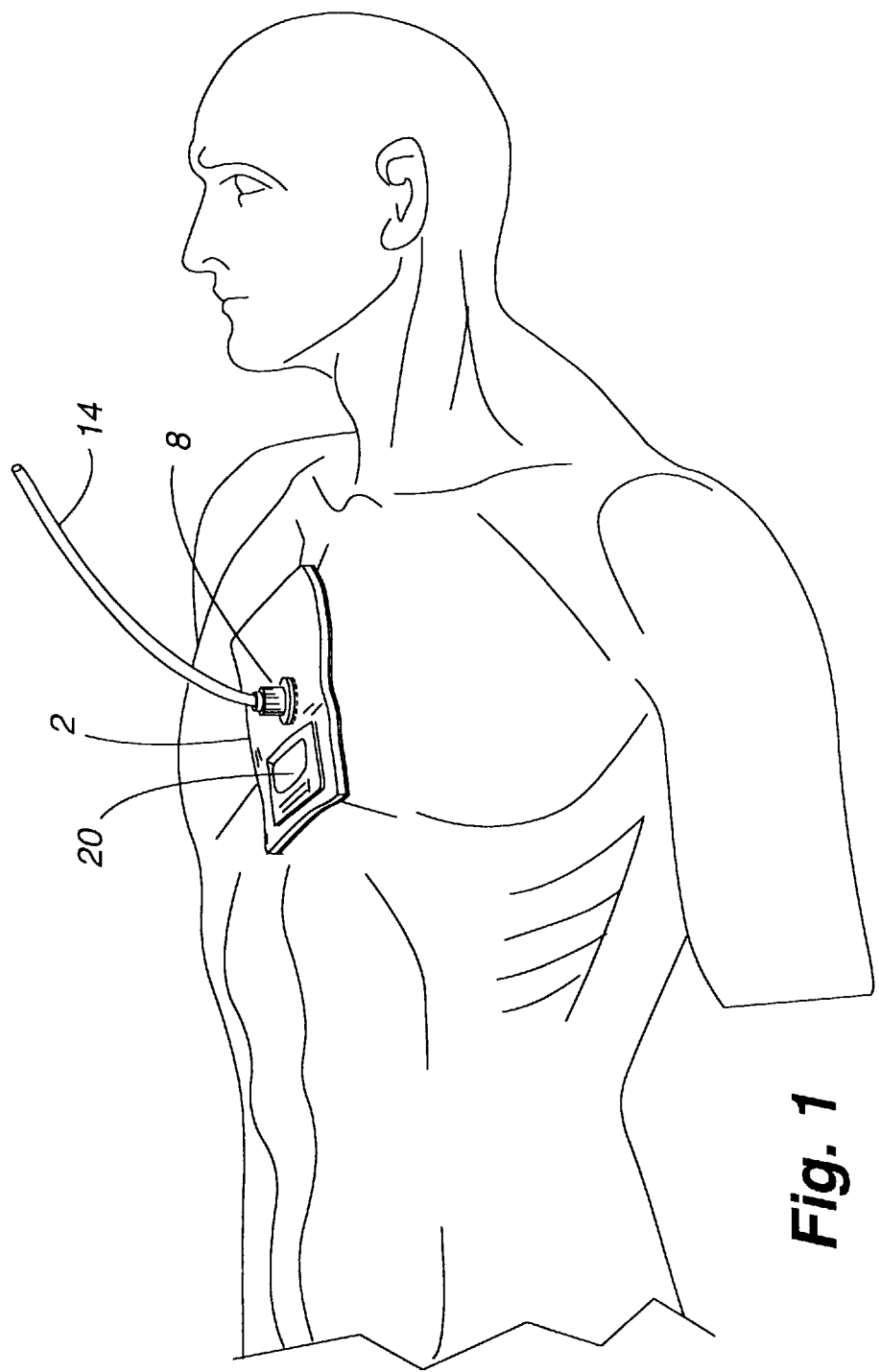
FIG. 1 is a perspective view of the medical catheter dressing device positioned over a patient's chest.
Figure 2:
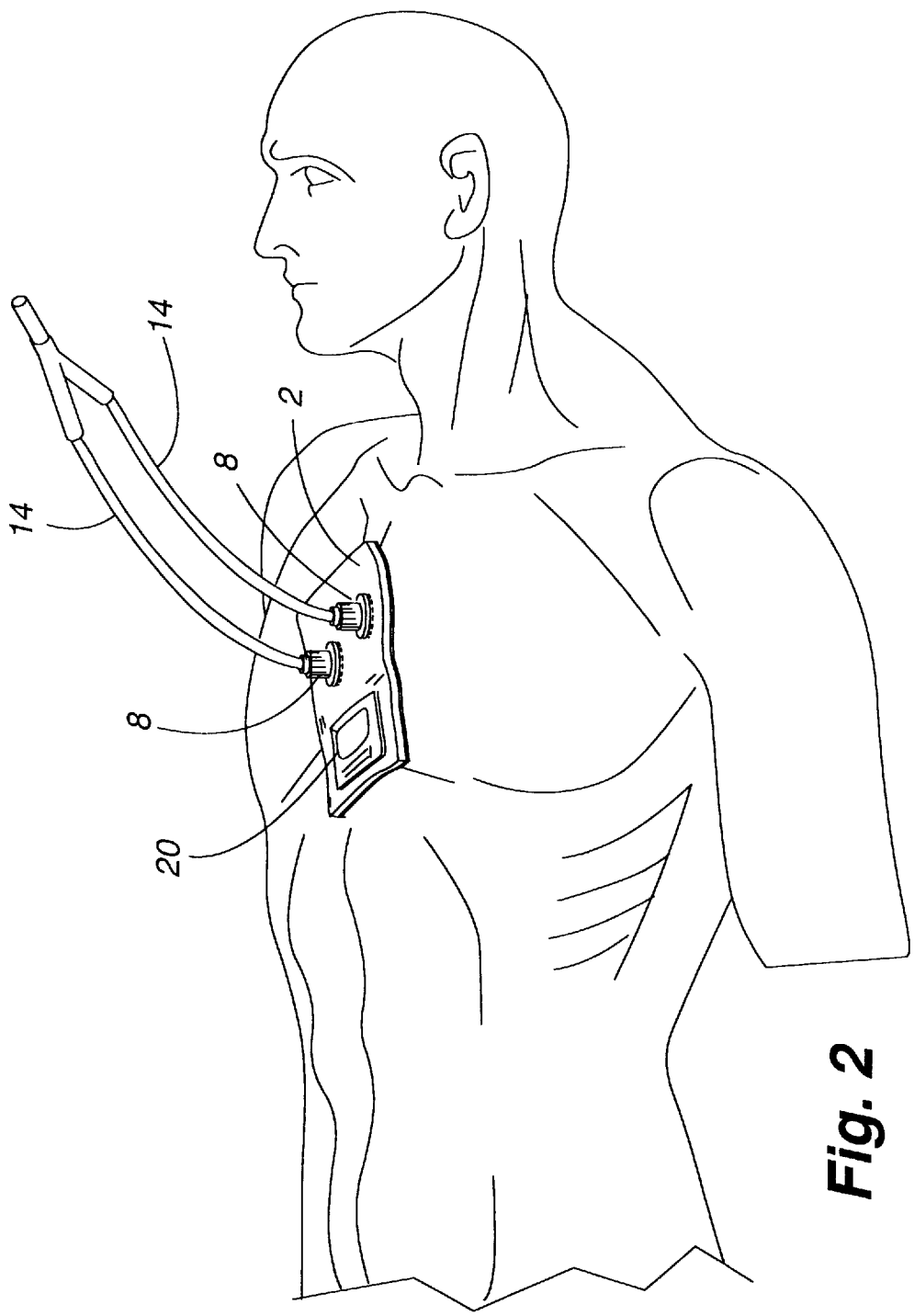
FIG. 2 is a perspective view of the medical catheter dressing device being used with dual catheter tubes.

Referring now to the drawings, FIG. 1 depicts the medical catheter dressing device positioned over the chest cavity of a patient and used in conjunction with a body conveyance tube 14. FIG. 2 shows an alternative embodiment of the present invention wherein the catheter dressing device is used in conjunction with two body conveyance tubes 14.

More particularly, the catheter dressing device comprises a dressing pad 2 temporarily interconnected to a patient's skin and having a conveyance tube 14 extending into a patient's body cavity. The conveyance tube 14 is supportably anchored to the patient's body by means of an upstanding retaining collar 8, which is removably interconnected to a top surface of the dressing pad 2. The upstanding retaining collar 8 is temporarily interconnected to the conveyance tube 14 to provide support to the conveyance tube 14 with adhesive tape 26, one or more O-rings 28 or by other similar interconnection means.

The upstanding retaining collar 8 is positioned over an access wound 32, through which the conveyance tube 14 is projected into the patient's body. An extensible biohazard control sleeve 16 is positioned within the retaining collar 8 and is used to contain medical biohazards such as blood in a confined space during removal of the conveyance tube 14 from the patient's body. After the retaining collar 8 and biohazard control sleeve 16 are disconnected from the top surface 4 of the dressing pad 2, a cover flap 20 may be used to removably cover the patient's access wound 32 to promote healing.

The dressing pad 2 is comprised of a flexible polymeric or woven material that provides a suitable barrier to contaminants and which may have properties conducive to wound healing. The dressing pad 2 is generally rectangular or square in shape with a sufficient surface area to provide support to the upstanding retaining collar and conveyance tube 14. As seen in FIGS. 1–4, the dressing pad is placed over a body cavity such as the pleural or mediastinal chest cavity and is positioned to support the conveyance tube 14 which extends into the body cavity.

The conveyance tube 14 is generally projected through a dressing pad aperture 34 which extends through the dressing pad top surface 4 to the dressing pad bottom surface 6. As seen in FIG. 2, in some applications two or more dressing pad apertures 34 may be required when more than one conveyance tube 14 is used. Alternatively, the dressing pad aperture 34 may be replaced with a slot (not shown) which extends from one edge of the dressing pad to substantially the center of the dressing pad. This allows the dressing pad 2 to be positioned proximate to and around the conveyance tube 14 without requiring the end of the conveyance tube 14 to be fed through the aperture 34 during the positioning of the dressing pad 2.

The bottom surface 6 of the dressing pad 2 is then temporarily attached to the skin of the patient by means of an adhesive. The adhesive may be sprayed directly onto the patient's skin, or more preferably may be pre-applied to the bottom surface 6 of the dressing pad 2 and protected from premature exposure to other surfaces with a release liner. In this application a pressure sensitive adhesive is attached to a polyolefin or polyvinyl substrate which comprises the bottom surface 6 of the dressing pad 2 and is covered with the release liner until use is desired. The release liner eliminates the need for spray adhesives or glues and hence is more suitable for a medical application. In the immediate area surrounding the aperture there is preferably an adhesive-free region to help prevent the bottom surface of the dressing pad 6 from adhering to the access wound 32.

The top surface 4 of the dressing pad 2 is generally comprised of a woven or non-woven material which facilitates the attachment of pressure sensitive adhesives. This is necessary in one embodiment to hold the retaining collar support ring 10 firmly yet removably to the top surface 4 of the dressing pad 2. To facilitate use, in one embodiment a release liner may be peeled from the bottom of the retaining collar support ring 10 to expose an adhesive which is pressed against the top surface 4 of the dressing pad 2. In an alternative embodiment a hook and loop type material such as Velcro™ may be used to removably interconnect the retaining collar support ring 10 to the top surface 4 of the dressing pad 2. In this embodiment an opposing section of the hook and loop type material must be interconnected to the dressing pad top surface 4 proximate the aperture 34 and opposed to the bottom surface 42 of the retaining collar support ring 10.

To assist in the disconnection of the retaining collar 8 from the dressing pad 2 after removal of the conveyance tube 14, a retaining collar pull tab 12 may be interconnected to the retaining collar support ring 10 as seen in FIGS. 3–7. The retaining collar pull tab 12 is generally comprised of a plastic or cloth strip or fiber material which has a surface area large enough to permit grasping for the removal of the retaining collar support ring 10.

In another embodiment of the present invention, the top surface 4 of the dressing pad 2 may have a control sleeve release ring 18 which is used to disconnect the biohazard control sleeve 16 from the dressing pad 2. The control sleeve release ring 18 may be comprised of a perforated strip which detaches from the dressing pad 2 upon finger pressure, or a release string (not shown) which is woven into the dressing pad material to disengage the control sleeve release liner 18 when pulled. The control sleeve release liner 18 allows the biohazard control sleeve 16 to be disconnected from the dressing pad 2 to expose the access wound 32, thus eliminating the need for the biohazard control sleeve 16 being removed with a knife or scissors.

Figure 5:
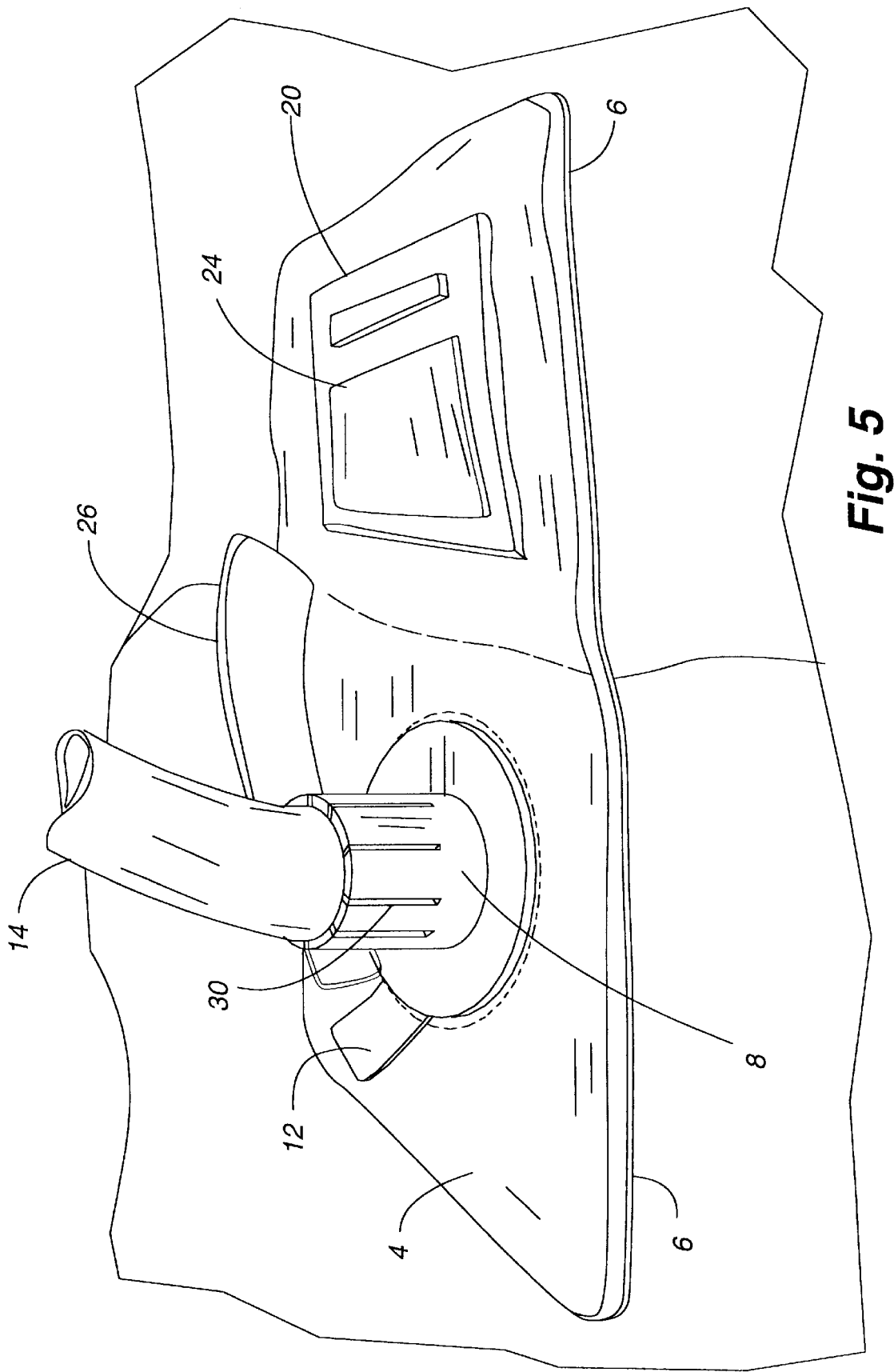
FIG. 5 is a perspective view of the medical catheter dressing device depicting the upstanding retaining collar, catheter and cover flap.
Figure 6:
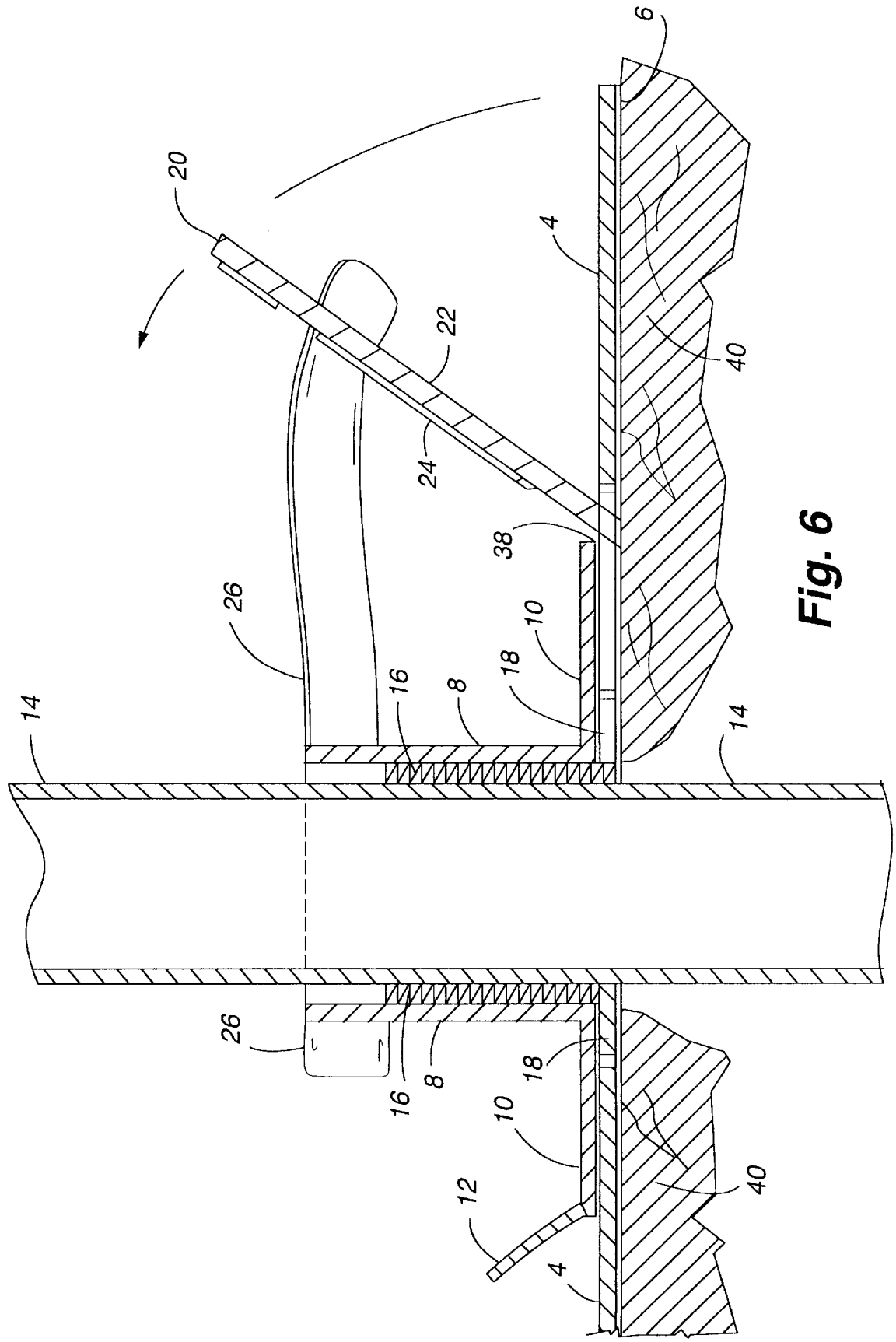
FIG. 6 is a cross-sectional view of the medical catheter dressing device with cover flap.

To promote healing of the access wound 32, the top surface of the dressing pad 2 may include a cover flap 20. The cover flap 20 may be hingably interconnected to the top surface 4 of the dressing pad 2 which prevents the cover flap from being inadvertently disconnected from the dressing pad 2. Referring now to FIGS. 5–7, the dressing pad cover flap 20 comprises a top surface 22 and bottom surface 24 which is extended over the access wound 32. To facilitate healing of the access wound 32 the bottom surface 24 of the cover flap 20 may be impregnated with an antibacterial or infection inhibiting medicated ointment. Furthermore, to prevent the cover flap 20 from becoming disengaged from the top surface 4 of the dressing pad 2, a pressure sensitive adhesive with release liner may be used for adherence to the top surface 4 of the dressing pad 2. Alternatively, hook and loop type materials such as Velcro™ may be used to temporarily interconnect the cover flap bottom surface 24 to the dressing pad top surface 4. Although the cover flap 20 is generally hingably interconnected to the top surface 4 of the dressing pad 2, in another embodiment the cover flap 20 may be removably disconnected from the top surface 4 of the dressing pad 2 to allow the cover flap 20 to be replaced with a new sterile cover flap 20 dressing.

As previously discussed, the conveyance tube 14 is supportably anchored to the top surface 4 of the dressing pad 2 by the use of an upstanding retaining collar 8. The retaining collar is generally comprised of a substantially rigid cardboard or plastic material with an internal diameter large enough to receive the conveyance tube 14. The upstanding retaining collar 8 has a top end extending upward and away from the dressing pad 2, and a bottom end interconnected to the retaining collar support ring 10, which is removably interconnected to the dressing pad top surface 4.

In one embodiment the retaining collar 8 may have a plurality of longitudinal slots 30 extending in the same general upward direction as the retaining collar 8. These longitudinal slots 30 may be seen in FIGS. 1–4. The longitudinal slots 30 allow the retaining collar 8 to operatively collapse around the conveyance tube 14 when external pressure is applied to the retaining collar 8. The external pressure is generally applied with an adhesive tape 26 (FIG. 5), or alternatively by the use of a semi-ridged ring (not shown) which can be extended over the retaining collar to supportably anchor the conveyance tube 14 to the upstanding retaining collar 8 and dressing pad 2. In one embodiment of the present invention as seen in FIG. 5, a predetermined length of adhesive tape 26 is partially interconnected to the upstanding retaining collar 8 to allow the adhesive tape 26 to be conveniently wrapped around the retaining collar 8 to temporarily interconnect the retaining collar 8 to the conveyance tube 14.

In an alternative embodiment the conveyance tube 14 may be supportably held to the retaining collar 08 by the use of one or more O-rings 28 as seen in FIG. 6. The O-rings 28 are generally interconnected to the internal surface of the retaining collar 8 near or proximate to the upper end of the retaining collar 8 and away from the retaining collar support ring 10. The O-rings 28 frictionally engage the exterior surface of the conveyance tube 14 and supportably anchor the conveyance tube 14 to the upstanding retaining collar 8. The O-rings 28 are typically comprised of a rubber or polymeric material and may have chevron type seals or other geometric configurations to provide support to the conveyance tube 14. Additionally, the O-rings 28 serve the purpose of substantially sealing circumferentially the space defined between the internal surface of the upstanding retaining collar 8 and the external surface of the conveyance tube 14. Thus, most if not all of the medical biohazards which are present during the removal of the conveyance tube 14 from the patient's access wound 32 are substantially contained within the upstanding retaining collar 8 and biohazard control sleeve 16 and thus not exposed to the attending medical staff.

Referring now to FIG. 7, in an alternative embodiment of the present invention, the upstanding retaining collar 8 may be oriented in relation to the skin surface at an acute angle, i.e., less than 90 degrees. This angle helps alleviate excessive stress on the access wound 32 and surrounding tissue and thus provides stability in certain applications where an artery, vein or body cavity is oriented more parallel to the skin surface. This orientation is particularly useful when using the catheter dressing device to introduce fluid into a patient's body, such as with percutaneous indwelling catheters. Preferably, the upstanding retaining collar orientation angle $\phi$ is between about 25 degrees and 75 degrees, and more preferably about 45 degrees.

Referring now to FIGS. 3–7, the present invention further utilizes a biohazard control sleeve 16 to contain medical biohazards discharged either from the conveyance tube 14 or access wound 32 during the removal of the conveyance tube 14 from the patient's body. More particularly, the biohazard control sleeve 16 may be comprised of an extendible pleated material which can be extended during removal of the conveyance tube 14 from the patient's body to contain any medical biohazards within the biohazard control sleeve 16. This containment helps prevent exposure to the medical staff of various medical biohazards such as blood and tissue.

The biohazard control sleeve 16 is generally cylindrical in shape and has a bottom end interconnected to the top surface of the dressing pad 2 proximate the patient's access wound 32. The top end of the biohazard control sleeve 16 is positioned near the upper one-third of the upstanding retaining collar 8, while the remainder of the biohazard control sleeve 16 is concealably stored within the internal diameter of the upstanding retaining collar 8. To permit significant extension, the biohazard control sleeve 16 is comprised of a pleated accordion type material which is substantially non-permeable to prevent medical biohazards from saturating or otherwise leaking through the biohazard control sleeve 16. For example, the biohazard control sleeve 16 may be comprised of polyvinyl chloride or a polyolefin material which can be pleated or folded in an accordion type fashion. Preferably, the biohazard control sleeve 16 can be extended between about four to twenty times their original folded length. This allows the biohazard control sleeve 16 to entirely envelop all of the conveyance tube 14 which has been positioned within the patient's body cavity.

Figure 3:
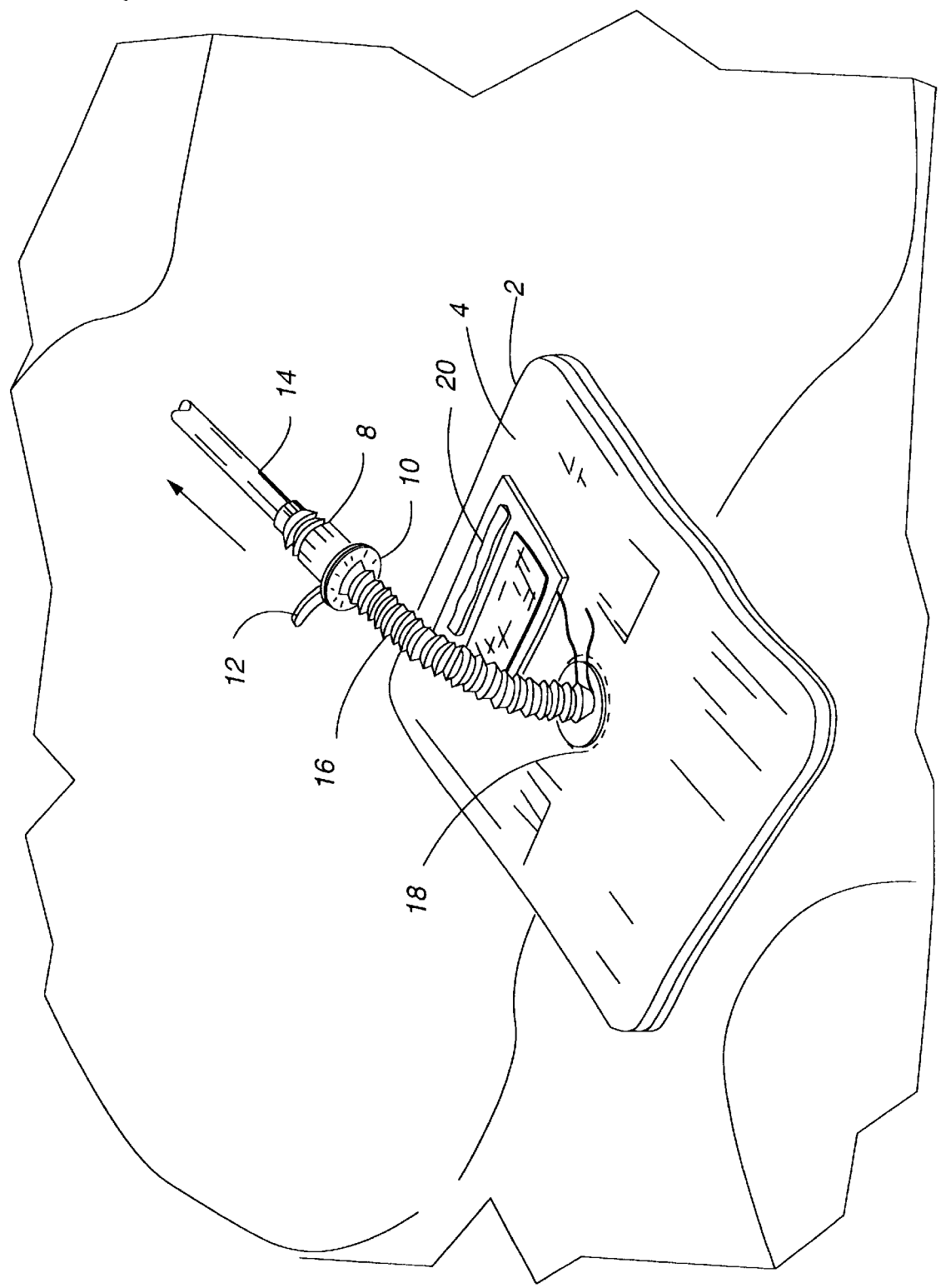
FIG. 3 is a perspective view of the medical catheter dressing device of FIG. 1 with extended biohazard control sleeve.
Figure 4:
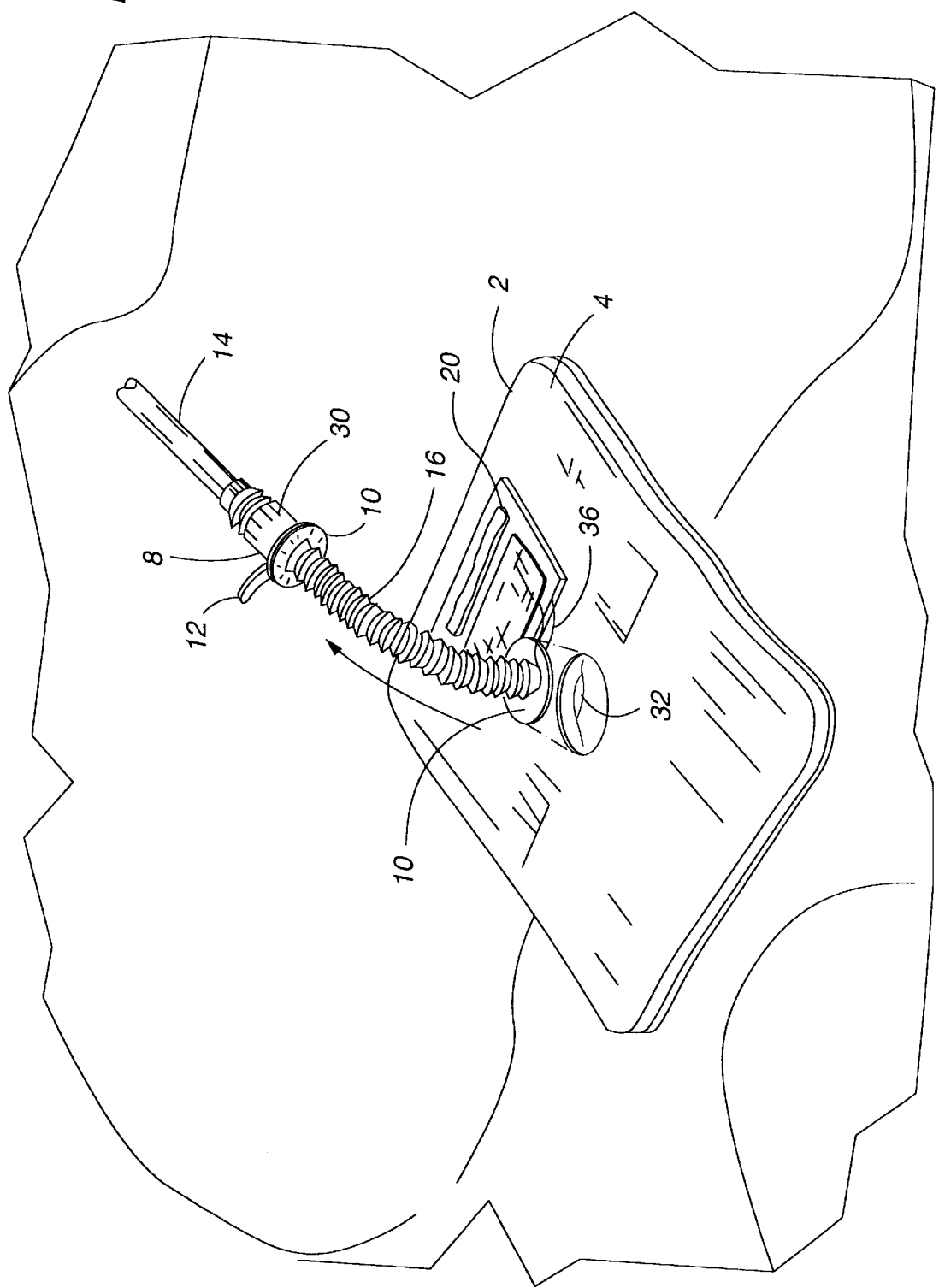
FIG. 4 is a perspective view of the medical catheter dressing device of FIG. 1 with a retaining collar support ring detached from the top surface of the dressing pad.

As seen in FIGS. 3–4, the biohazard control sleeve 16 is extended away from the patient's body as the upstanding retaining collar 8 is disconnected and pulled away from the top surface of the dressing pad 2. As the inlet end of the conveyance tube 14 is removed from the patient's body, the conveyance tube 14 is contained within the biohazard control sleeve 16, thus substantially inhibiting the exposure of medical biohazards to attending medical personnel.

In a preferred embodiment of the present invention, one or more drawstrings 31 may be attached to the bottom and/or top ends of the biohazard control sleeve 16 to help contain any medical biohazards therein. Upon removal of the inlet end of the conveyance tube 14 from the patient's body, the drawstring 36 is cinched tightly to substantially contain any medical biohazards within the biohazard control sleeve 16. The biohazard control sleeve 16 may then either be cut with a knife or scissors below the drawstring and proximate to the top surface 4 of the dressing pad 2, or the biohazard control sleeve release ring 18 may be used to disconnect the biohazard control sleeve 16 from the dressing pad 2 (FIG. 4), exposing the access wound 32.

Figure 9:
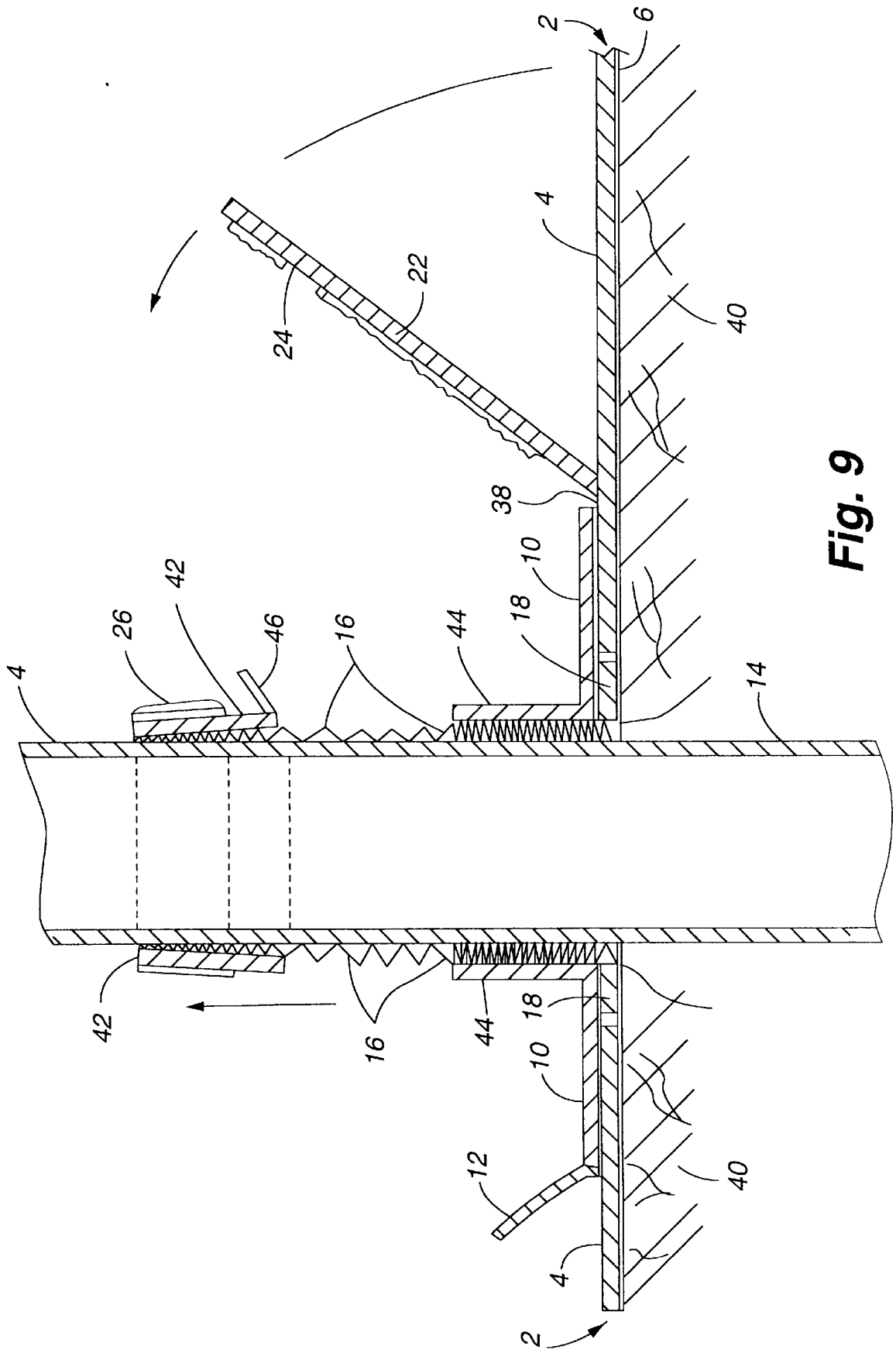
FIG. 9 is a cross-sectional view of the medical catheter device showing the retaining collar upper section disconnected from the retaining collar lower section and the biohazard control sleeve partially extended.

In an alternative embodiment of the present invention shown in FIG. 9, the upstanding retaining collar may further comprise a retaining collar upper section 42 removably interconnected to a retaining collar lower section 44. The retaining collar upper section 42 and lower section 44 may be releasably interconnected with a retaining collar release tab 46. In this embodiment, the biohazard control sleeve 16 is interconnected on a lower end to the dressing pad 2 and on an opposing end to the retaining collar upper section 42. The biohazard control sleeve 16 may be interconnected at the bottom of the retaining collar upper section 42 or at other operative locations on the retaining collar upper section 42. Thus, FIG. 9 is only illustrative of one particular embodiment and other effective designs may also be implemented to accomplish the same purpose.

To remove the conveyance tube 14 from the patient's body, the retaining collar upper section 42 is disconnected from the retaining collar lower section 44 by means of the retaining collar release tab 46. For example, the retaining collar release tab 46 may be interconnected to a string or wire interwoven into the retaining collar 8 to allow the retaining collar upper section 42 to be disconnected from the retaining collar lower section 44.

After disconnection of the retaining collar upper section 42 and lower section 44, the retaining collar upper section 42 is pulled away from the retaining collar lower section 44, which remains removably interconnected to the dressing pad top surface 4. As the retaining collar upper section 42 is pulled away from the patient's body, the biohazard control sleeve 16 is extended upwardly away from the patient's body, while simultaneously enclosing the conveyance tube 14 and any medical biohazards discharged therein. Upon complete removal of the conveyance tube 14 above the retaining collar lower section 44, the biohazard control sleeve 16 may be closed with a drawstring, clip or other device above the retaining collar lower section 44. The biohazard control sleeve 16 is then cut with a knife or other sharp instrument to permit the removal and proper disposal of the retaining collar upper section 42, biohazard control sleeve 16 and conveyance tube 14. The retaining collar lower section 44 may then be removed from the dressing pad top surface 4 by pulling the retaining collar pull tab 12. Alternatively, rather than cutting the biohazard control sleeve 16 after the conveyance tube 14 is withdrawn above the retaining collar lower section 44, the pull tab 12 can be used to disconnect the retaining collar lower section 44 from the dressing pad 2, wherein the biohazard control sleeve 16 can either be severed near the access wound or removed by utilizing the biohazard control sleeve release ring 18.

In practice, the medical catheter dressing device is utilized by the physician making an incision in the patient's skin surface and surrounding tissue to expose a body cavity, artery or vein. The inlet end of a conveyance tube 14 is then introduced into the patient's body to facilitate the introduction and/or removal of liquids, solids and gases from the patient's body.

The exit end of the conveyance tube 14 is then extended through an aperture 34 in the dressing pad 2, which has a removably interconnected upstanding collar positioned around the aperture 34. The bottom surface 6 of the dressing pad 2 is then temporarily attached to the patient's skin 40 by means of a spray adhesive or with adhesive preattached to the bottom surface 4 of the dressing pad 2.

The conveyance tube 14 is then securably interconnected to the retaining collar 8 by utilizing an adhesive tape 26 wrapped tightly around the retaining collar 8. Alternatively, one or more O-rings 28 may be used independently or in conjunction with the adhesive tape to secure the conveyance tube 14 to the retaining collar 8. Thus, the conveyance tube 14 is now securely anchored to the upstanding retaining collar 8 and dressing pad 2.

Upon completion of the removal and/or introduction of fluids through the conveyance tube 14, the retaining collar support ring 10 is disconnected from the top surface of the dressing pad 2. This may be accomplished by the use of a pull tab 12. Alternatively, the retaining collar upper section 42 may be removed from the retaining collar lower section 44 by pulling a retaining collar release tab 46. In either embodiment, as the physician pulls the retaining collar 8 away from the patient's body, the conveyance tube 14 is gradually removed from the patient's body through the access wound 32.

As the conveyance tube 14 is removed from the patient's body, the biohazard control sleeve 16 is progressively extended to enclose the conveyance tube 14. Thus, medical biohazards are contained within the biohazard control sleeve 16. Once the inlet end of the conveyance tube 14 is pulled through the access wound 32, a drawstring 36 may be utilized to tighten and further contain any medical biohazards within the biohazard control sleeve 16.

The attending medical personnel may then either cut the biohazard control sleeve 16 near the top surface 4 of the dressing pad 2, or release the biohazard control sleeve 16 from the dressing pad 2 with the control sleeve release collar. In either event, the access wound 32 is now exposed for proper cleaning and/or wound closure by means of sutures, staples or other wound closure devices known in the art.

To promote healing, a cover flap 24 may be extended over the access wound 32 to prevent contaminants from coming into contact with the access wound 32. The cover flap may be periodically replaced or retracted as necessary to monitor the healing of the access wound 32.

For reference purposes, the following is a detailed list of the described components of the medical catheter dressing device, and corresponding numbers as shown in the drawings:

| Number | Component |
| --- | --- |
| 2 | Dressing pad |
| 4 | Dressing pad top surface |
| 6 | Dressing pad bottom surface |
| 8 | Retaining collar |
| 10 | Retaining collar support ring |
| 12 | Retaining collar pull tab |
| 14 | Conveyance tube |
| 16 | Biohazard control sleeve |
| 18 | Biohazard control sleeve release ring |
| 20 | Cover flap |
| 22 | Top surface of cover flap |
| 24 | Bottom surface of cover flap |
| 26 | Adhesive tape |
| 28 | O-rings |
| 30 | Longitudinal slots |
| 32 | Access wound |
| 34 | Dressing pad aperture |
| 36 | Drawstring |
| 38 | Retaining collar adhesive surface |
| 40 | Patient's skin |
| 42 | Retaining collar upper section |
| 44 | Retaining collar lower section |
| 46 | Retaining collar release tab |

The foregoing description of the present invention has been presented for purposes of illustration and description. The description is not intended to limit the invention to the form disclosed herein. Consequently, the invention modification commensurate with the above teachings and skill and knowledge of the relevant art are within the scope of the present invention. The preferred embodiment described above is also intended to explain the best mode known of practicing the invention and to enable others skilled in the art to utilize the invention in various embodiments with the various modifications required by their particular applications for use in the invention. It is intended that the appended claims be construed to include all alternative embodiments as permitted by the prior art.

What is claimed is:

1. A medical dressing assembly for use with at least one conveyance tube positionable in a patient's body for the removal or injection of fluid or solid matter therethrough, comprising:

a dressing pad selectably attachable to said patient adjacent one or more access wounds for penetration of said conveyance tubes, said dressing pad having at least one aperture extending therethrough to receive said conveyance tubes;

an upstanding retaining collar positioned adjacent to each of said apertures for selective interconnection to said body matter conveyance tubes and interconnectable to said dressing pad, wherein said retaining collar and said dressing pad supportably anchor said body matter conveyance tubes; and an biohazard control sleeve having a bottom end interconnected to said dressing pad proximate said apertures, and a top end selectively extendable away from said apertures, wherein said biohazard control sleeve is progressively receivable within said retaining collar permitting withdrawal of said body matter conveyance tube from said access wound of said patient's body while enclosing said fluid or solid matter or other medical biohazards from said patient's body within said biohazard control sleeve wherein said sleeve is extendable along its longitudinal axis.

2. The dressing assembly of claim 1, wherein a bottom surface of said dressing pad comprises a pressure sensitive adhesive.

3. The dressing assembly of claim 1, further comprising an interconnection means for interconnecting said retaining collar to said body matter conveyance tube.

4. The dressing assembly of claim 3, wherein said interconnection means comprises adhesive tape.

5. The dressing assembly of claim 3, wherein said interconnection means comprises an o-ring positioned proximate an interior surface of said retaining collar.

6. The dressing device of claim 1, wherein said retaining collar is removably interconnected to a top surface of said dressing pad with a hook and loop type interface material.

7. The dressing assembly of claim 1, wherein said retaining collar is removably interconnected to a top surface of said dressing pad with an adhesive layer.

8. The dressing assembly of claim 1, wherein said retaining collar is disengaged from said top surface of said dressing pad with at least one pull tab.

9. The dressing assembly of claim 1, wherein said biohazard control sleeve is releasably interconnected to said dressing pad with a perforated release mechanism.

10. The dressing assembly of claim 1, wherein said biohazard control sleeve further comprises one or more interconnected drawstrings for containing said body matter within said biohazard control sleeve.

11. The dressing assembly of claim 1, wherein said biohazard control sleeve has a sufficient length to receive upon withdrawal the entire length of said body matter conveyance tube positioned within said patient's body.

12. The dressing assembly of claim 1, wherein said upstanding retaining collar is comprised of a flexible material with a plurality of longitudinal slots, wherein said collar is collapsible around said conveyance tube.

13. The dressing assembly of claim 1, wherein said upstanding retaining collar is oriented in relation to said dressing pad at an angle less than about 90 degrees.

14. The medical dressing assembly of claim 1, wherein said upstanding retaining collar further comprises an upper member removably interconnected to a lower member, said upper member operably attached to said extendable biohazard control sleeve, wherein when said upper member is disconnected from said lower member and pulled away from said patient's body, said biohazard control sleeve is extended upward and around said conveyance tube as said conveyance tube is withdrawn from said patient's body.

15. The dressing assembly of claim 1, wherein said dressing pad further comprises a cover flap having a sufficient dimension to cover said access wound upon removal of said retaining collar.

16. The dressing assembly of claim 15, wherein said cover flap is interconnectable to said dressing pad.

17. The dressing assembly of claim 15, wherein said cover flap comprises a top surface and a bottom surface, said bottom surface containing a medicated ointment to promote healing of said access wound.

18. A medical method of managing one or more body conveyance tubes used for injecting or removing fluid or solid matter from a patient's body, comprising the steps of:

(a) inserting an inlet end of said body conveyance tube into said patient's body through one or more access openings;

(b) positioning a dressing pad assembly around said body conveyance tubes, said assembly comprising a dressing pad, an upstanding collar interconnected to said dressing pad and an extendable biohazard control sleeve operably located proximate said access openings;

(c) securing said body conveyance tube to said upstanding collar;

(d) anchoring a bottom surface of said dressing pad to said patient's skin wherein said body conveyance tube is supportably positioned to said patient's body;

(e) passing said fluid or solid matter through said body conveyance tubes; and (f) removing said body conveyance tubes from within said patient's body while progressively extending said biohazard control sleeve away from said access opening, wherein said fluid or solid matter in said conveyance tube and medical biohazards from said patient's body are substantially contained within said biohazard control sleeve.

19. The method of claim 18, further comprising the step of detaching said upstanding collar from said dressing pad, wherein said biohazard control sleeve, said collar and said body conveyance tube are progressively removed away from said access openings simultaneously.

20. The method of claim 18, further comprising the step of extending one or more cover flaps interconnectable to said dressing pad over said access wounds after removing said body conveyance tubes from said patient's body.

21. The method of claim 18, wherein said step of anchoring said bottom surface of said dressing pad to said patient's skin comprises applying an adhesive to said patient's skin.

22. The method of claim 18, further comprising the step of capturing said fluid and said solid matter draining from said conveyance tube and any medical biohazards discharged from said access opening within said biohazard control sleeve upon removal of said body conveyance tube from said patient's body.

23. The method of claim 18, wherein said step of positioning comprises passing an outlet end of said body conveyance tubes through an aperture extending through said dressing pad.

24. The method of claim 18, further comprising the step of detaching said biohazard control sleeve from said dressing pad after removal of said body conveyance tube from said patient's body.

25. A medical dressing assembly for use with one or more body conveyance tubes positioned in a patient's body for the transfer of fluid and solid matter therethrough, comprising:
- a dressing pad selectably attachable to said patient's body adjacent one or more access wounds for penetration of said body conveyance tubes, said dressing pad having one or more apertures extending therethrough to receive said conveyance tubes;
- an upstanding retaining collar positioned adjacent to each of said apertures for selective interconnection to said conveyance tube and removably interconnected to said dressing pad, wherein said retaining collar and said dressing pad supportably anchor said conveyance tube to said patient's body;
- an biohazard control sleeve having a bottom end interconnected to said dressing pad proximate said aperture, and a top end selectively extendable away from said aperture, wherein said biohazard control sleeve is progressively receivable within said retaining collar permitting withdrawal of said conveyance tubes from said access wounds of said patient's body while substantially containing said fluid and solid matter and medical biohazards from said patient's body within said biohazard control sleeve; and wherein said sleeve is extendable along a longitudinal axis,
- at least one cover flap interconnectable to a top surface of said dressing pad, wherein said cover flaps may be removably positioned over said access wounds to promote the healing of said access wounds upon removal of said conveyance tube and said biohazard control sleeve.

26. The medical dressing assembly of claim 25, wherein said upstanding retaining collar is removably interconnected to said top surface of said dressing pad with an adhesive material.

27. The medical dressing assembly of claim 25, wherein said biohazard control sleeve is comprised of an extensible polymeric material.

28. The medical dressing pad of claim 25, wherein said biohazard control sleeve has a cylindrical cross-sectional shape.

29. The medical dressing assembly of claim 25, further comprising at least one drawstring interconnected to said biohazard control sleeve to substantially contain said fluid or solid matter or any medical biohazards within said biohazard control sleeve during removal of said conveyance tube from said patient's body.

30. The medical dressing assembly of claim 25, further comprising at least one clip removably interconnected to said biohazard control sleeve to substantially contain said fluid or solid matter or any medical biohazards within said biohazard control sleeve during removal of said conveyance tube from said patient's body.

* * * * *